United States Patent [19]

Steiner et al.

[11] Patent Number: 5,679,823

[45] Date of Patent: Oct. 21, 1997

[54] METHOD OF PRODUCING ALKYL HALOGEN SILANES

[75] Inventors: Matthias-Sven Steiner; Christoph Schild, both of Leverkusen; Bruno Degen, Much, all of Germany

[73] Assignee: Bayer Aktiengesellschaft, Leverkusen, Germany

[21] Appl. No.: 703,242

[22] Filed: Aug. 26, 1996

[30] Foreign Application Priority Data

Sep. 1, 1995 [DE] Germany ............ 195 32 315.7

[51] Int. Cl.$^6$ ........................................ C07F 7/16
[52] U.S. Cl. ........................................ 556/472; 556/473
[58] Field of Search ........................ 556/472, 473

[56] References Cited

U.S. PATENT DOCUMENTS

| Re. 33,452 | 11/1990 | Ward et al. |
|---|---|---|
| 2,380,995 | 8/1945 | Rochow . |
| 2,904,574 | 9/1959 | Kohn et al. ............ 556/472 |
| 4,487,950 | 12/1984 | Ward, III et al. |
| 4,500,724 | 2/1985 | Ward, III et al. |
| 4,762,940 | 8/1988 | Halm et al. |
| 5,015,751 | 5/1991 | Feldner et al. |
| 5,059,706 | 10/1991 | Degen et al. ............ 556/472 |
| 5,334,738 | 8/1994 | Pachaly et al. |
| 5,500,399 | 3/1996 | Faure et al. |

FOREIGN PATENT DOCUMENTS

| 0223447 | 5/1987 | European Pat. Off. |
|---|---|---|
| 0391133 | 10/1990 | European Pat. Off. |
| 0522844 | 1/1993 | European Pat. Off. |
| 0610807 | 8/1994 | European Pat. Off. |
| 0673880 | 9/1995 | European Pat. Off. |
| 0685428 | 12/1995 | European Pat. Off. |
| 3501085 | 8/1985 | Germany . |
| 4037021 | 4/1994 | Germany . |
| 2153697 | 8/1985 | United Kingdom . |

OTHER PUBLICATIONS

N.P. Lobusevich, et al., Influence of Additions of Some Elements to Silicon–Copper Alloys on Their Activity in the Reaction With Methyl Chloride, pp. 2727–2729, Aug. 1964.

N.P. Lobusevich, et al., "Influence of Sulfur Dioxide on the Synthesis of Methylchlorosilanes", pp.1844–1846, Aug. 1965.

*Primary Examiner*—Paul F. Shaver
*Attorney, Agent, or Firm*—Sprung Horn Kramer & Woods

[57] ABSTRACT

A method of producing alkyl halogen silanes, more particularly methyl chlorosilanes, by reacting silicon with an alkyl halide in the presence of at least one catalyst and easily volatile or gaseous halogen-containing and/or alkoxy-containing sulphur compound and optional promoter substances.

5 Claims, No Drawings

METHOD OF PRODUCING ALKYL HALOGEN SILANES

The invention relates to a method of producing alkyl halogen silanes by reacting silicon with an alkyl halide in the presence of at least one catalyst and easily volatile or gaseous halogen-containing and/or alkoxy-containing sulphur compound and optionally at least one additional promoter substances. More particularly the invention relates to a method of producing methyl chlorosilanes.

The principal method of producing methyl chlorosilanes is by direct reaction between pulverized silicon and methyl chloride in the presence of a copper catalyst. The reaction is known as the "Rochow Synthesis" and is described in U.S. Pat. No. 2,380,995.

This method yields a mixture of methyl chlorosilanes, in which dimethyl dichlorosilane is the main component. Methyl trichlorosilane is also formed together with other substances such as trimethyl chlorosilane, tetra-methyl silane, methyl hydrogen dichlorosilane and higher-boiling methyl chlorodisilanes.

Since the synthesis was discovered, there have been numerous efforts to improve the method of synthesis and increase the proportion of dimethyl dichlorosilane, i.e. to guide the synthesis as far as possible so as to be selective with regard to formation of dimethyl dichlorosilane.

This object is achieved mainly by conforming to purity criteria regarding the raw materials and by controlled use of promoters. Zinc, tin and phosphorus, either elementary or in the form of their compounds, are examples of known promoters (e.g. EP-A 223 447).

Zinc and optionally tin and also volatile phosphorus compounds are used as promoters (see EP-A 391 133). Phosphorus-containing contact substances, however, have the disadvantage that the production rate is relatively low even in the presence of additional promoters, and there is an excessive content of methyl dichlorosilane, which indicates undesirable cracking of the mixture of methyl chloride and alkyl chlorosilane.

The object of the invention therefore is to provide a method of producing alkyl chlorosilanes characterized by high selectivity, a low content of methyl hydrogen dichlorosilane (MeH) and a high production rate. The measure of selectivity given in the literature is usually the ratio of methyl trichloromethylsilane to dimethyl dichlorosilane (Tri/Di).

It has now unexpectedly been discovered that if easily volatile or gaseous halogen-containing and/or alkoxy-containing sulphur compounds are used these requirements can be satisfied and also a good (Tri/Di) ratio and a reduced content of high-boiling constituents can be obtained.

This is all the more astonishing in that S and $SO_2$ in the literature are frequently described as catalyst poisons (N. P. Lobusevich et at., Zhurnal Obshchei Khimii, Vol. 34, pages 2706–2708 (1964), Zhurnal Prikladnoi Khimii, Vol. 38, No. 8, page 1884 (1965)).

The invention therefore relates to a method of producing alkyl halogen silanes by reacting silicon with an alkyl halide in the presence of at least one catalyst, wherein the reaction is brought about in the presence of an easily volatile or gaseous halogen-containing and/or alkoxy-containing sulphur compound and optionally additional promoter substances.

Easily volatile or gaseous halogen-containing and/or alkoxy-containing sulphur compounds according to the invention are compounds having the formula I $$S_aO_bX_c \qquad (I)$$

in which

X is F, Cl, Br, I or $C_{1-18}$-alkoxy and polysulphur with a>2 compounds thereof.

| X is | a | b | c |
|---|---|---|---|
| F, then | 1 or 2 | 0 or 1 or 2 | 2<br>4 for b = 0<br>6 for a = 1 and b = 0<br>10 for a = 2 and b = 0 |
| Cl, then | 1 or 2 | 0 or 1 or 2 | 2<br>4 for a = 1 and b = 0 |
| Br, then | 1 or 2 | 0 or 1 | 2 |
| I, then | 2 | 0 | 2 |
| $C_1$–$C_{18}$-alkoxy preferably $C_1$–$C_8$-alkoxy, then | 1 | 1 or 2 | 2 |

X in the molecule may also denote a combination of various halogen and/or alkoxy radicals.

The easily volatile or gaseous halogen-containing and/or alkoxy-containing sulphur compounds can be produced by known methods, also in situ. By easily volatile are meant compounds having a boiling point of no more than 300° C., preferably no more than about 150° C.

Particular preference is given to $SOCl_2$, $SO_2Cl_2$, $SCl_2$ and/or $S_2Cl_2$, especially $SOCl_2$.

The catalyst according to the invention can be any conventional copper catalyst, such as the following: partly oxidized copper ($Cu°/Cu_2O/CuO$) (U.S. Pat. No. 4,500,724), mixtures of metallic copper and $Cu_2O$ /CuO DE-A 3 501 085), $Cu_2Cl_2$, $CuCl_2$ (U.S. Pat. No. 4,762,940), Cu formate (U.S. Pat. No. 4,487,950), etc. It is preferable to use partly oxidized copper ($Cu°/Cu_2O/CuO$). The copper catalyst is used preferably in a proportion of 0.05 to 10 wt.%, particularly preferably 0.1–7 wt.% relative to silicon.

The silicon used according to the invention can have a purity of >95%. Silicon with >98% purity is preferred. The particle size of the silicon is arbitrary but is preferably between 50 and 500 μm.

The silicon used can also be: atomized silicon according to U.S. Pat. No. 50,15,751 or structurally optimized silicon according to EP-A 610 807, or silicon produced according to EP-A 673 880 or EP-A 522 844.

Special types of silicon such as for example those described in DE-A 40 37 021 or EP-A 685 428, can also be used.

The alkyl halides according to the invention can be any conventional $C_1$–$C_8$ alkyl halides, preferably methyl chloride.

Of course, use of easily volatile or gaseous halogen-containing and/or alkoxy-containing sulphur compounds does not exclude additional use of other known promoter substances such as zinc or zinc compounds, aluminum or aluminum compounds, tin or tin compounds or phosphorus or phosphorus compounds, alone or in combination.

Preference is given to tin, aluminum, phosphorus or zinc, alone or in combination, in elementary form or in the form of their compounds.

The term "compound" includes alloys.

The promoters, if present, are preferably added in the following proportions:

Tin: 5–200 parts per 1 000 000 parts silicon and/or

Zinc: 10–10 000 parts per 1 000 000 parts silicon and/or

Aluminum: 0.01–1 wt.% relative to silicon and/or

Phosphorus: 20–2500 parts per 1 000 000 parts silicon.

The method is preferably carried out in the normal temperature and pressure range for Rochow synthesis.

A temperature between 280° and 390° C. and a pressure of 1 to 10 bar is preferred.

In the preferred method of working the invention, the desired quantity of easily volatile or gaseous halogen-containing and/or alkoxy-containing sulphur compound is added discontinuously at short intervals or continuously to the alkyl halide, which is continuously conveyed over the contact material. The amount used in a discontinuous test (e.g. in the laboratory) will depend on the amount of contact material but in a continuous process it advantageously depends on the amount of fresh contact material, which is usually topped up, likewise continuously, in the reactor. The easily volatile or gaseous halogen-containing and/or alkoxy-containing sulphur compounds are distributed in optimum manner via the gas phase. The proportion is between 5 and 2000 ppm, preferably between 10 and 500 ppm relative to the contact material. These figures are relative to the sulphur content of the sulphur compound used.

The method according to the invention is not restricted to a particular technique of direct synthesis. For example the reaction can be discontinuous or continuous, using a fluidized bed or agitated bed or solid bed.

The advantages of using easily volatile gaseous halogen-containing and/or alkoxy-containing sulphur compounds, as shown in the following examples, is that the proportion of high-boiling constituents is reduced, a good (Tri/Di) ratio is obtained, and there is a marked reduction in the proportion of MeH and a high production rate.

The following examples will illustrate the invention in greater detail but are in no way limitative (percentages are given by weight).

EXAMPLES

The following experiments were carried out in a glass agitated-bed reactor, inner diameter 30 mm, equipped with a spiral agitator. The silicon used had a purity of 98.8% and a particle size distribution of 71–160 μm.

The contact material consisted of 40 g silicon, 3.2 g copper catalyst and 0.05 g ZnO and was homogenized before use.

Methyl chloride at a pressure of 2 bar was conveyed from below via a glass frit through the contact material. The flow rate of methyl chloride was kept constant and in all cases was about 1.8 l/h. After travelling through the induction phase, a steady-state test phase was set at 300° C. The amount of crude silane formed per unit time was determined under these conditions. The individual constituents were determined by gas chromatography. The stated values are averages each from four individual measurements in each of two runs.

Example 1

Example 1 demonstrates the effect of various halogen- and/or alkoxy-containing sulphur compounds on the results obtained in the Rochow synthesis. The selected compounds were $SOCl_2$ and $S_2Cl_2$.

Silicon having the following characteristic data: Al: 0.095%; Ca: 0.048%; Fe: 0.50; Ti: 0.023% was used. Test 5 was carried out as a comparative test without the addition of halogen- and/or alkoxy-containing sulphur compounds.

TABLE 1

The addition of halogen- and/or alkoxy-containing sulphur compounds to the contact material

| test no. | sulphur added [ppm] | sulphur compound | production rate [g/h][1] | MeH [%][1] | Di[%][1] | Tri/Di[1] | PB[%][2] |
|---|---|---|---|---|---|---|---|
| 1 | 50 | $SOCl_2$ | 6.0 | 1.7 | 88.9 | 0.071 | 1.6 |
| 2 | 100 | $SOCl_2$ | 6.1 | 1.3 | 90.5 | 0.062 | 1.8 |
| 3 | 200 | $SOCl_2$ | 6.8 | 1.6 | 89.2 | 0.070 | 1.4 |
| 4 | 200 | $S_2Cl_2$ | 6.8 | 1.6 | 88.6 | 0.73 | 1.6 |
| 5 | — | — | 4.6 | 2.0 | 89.0 | 0.067 | 1.3 |

[1] MeH: methyl hydrogen dichlorosilane $MeHSiCl_2$; Di: dichloromethylsilane $Me_2SiCl_2$; Tri/Di (trichloromethylsilane $MeSiCl_3$/dichlorodimethylsilane $Me_2SiCl_2$); the percentages (% by weight) are based on the monomers obtained
[2] PS: polysiloxanes [boiling point (at 1013 mbar) >80° C.], the percentage relates to the total quantity of silane mixture formed.

Table 1 demonstrates that the use of halogen- and/or alkoxy-containing sulphur compounds by themselves reduces the percentage of MeH and of high-boiling compounds in the product spectrum and has a positive effect on the production rate.

Example 2

This example demonstrates the effect of a combination of halogen- and/or alkoxy-containing sulphur compounds ($SOCl_2$ was selected as an example) and phosphorus (e.g. in the form of $PCl_3$) on the results obtained in the Rochow reaction.

The same silicon was used as in Example 1.

TABLE 2

The addition of halogen- and/or alkoxy-containing sulphur compounds and phosphorus to the contact material

| test no. | sulphur added [ppm] | phosphorus added [ppm] | production rate [g/h][1] | MeH [%][1] | Di[%][1] | Tri/Di[1] | PS [%][2] |
|---|---|---|---|---|---|---|---|
| 5 | — | 50 | 5.7 | 2.3 | 88.5 | 0.069 | 1.1 |
| 6 | — | 100 | 4.0 | 2.0 | 90.1 | 0.059 | 2.1 |
| 7 | 50 | 50 | 6.3 | 2.0 | 89.3 | 0.065 | 1.6 |
| 8 | 100 | 100 | 4.6 | 1.7 | 90.8 | 0.056 | 0.7 |

[1] MeH: methyl hydrogen dichlorosilane $MeHSiCl_2$; Di: dichlorodimethylsilane $Me_2SiCl_2$; Tri/Di: (trichloramethylsilane $MeSiCl_3$/dichlorodimethylsilane $Me_2SiCl_2$); the percentages (% by weight) are based on the monomers obtained
[2] PS: polysiloxanes [boiling point (at 1013 mbar) >80° C.], the percentage relates to the total quantity of silane mixture formed The results in Table 2 demonstrate that, in the presence of phosphorus-containing promoters, halogen- and/or alkoxy-containing sulphur compounds increase the production rate, lower the percentage of MeH and high-boiling compounds and also produce an improved tri-di ratio.

Example 3

This example demonstrates the effect of a combination of halogen- and/or alkoxy-containing sulphur compounds ($SOCl_2$ was selected as an example) and tin (for example in the form of metallic tin) on the results obtained in the Rochow reaction.

The same silicon was used as in Example 1.

TABLE 3

The addition of halogen- and/or alkoxy-containing sulphur compounds and tin to the contact material

| test no. | sulphur added [ppm] | tin added [ppm] | production rate [g/h][1] | MeH [%][1] | Di[%][1] | Tri/Di[1] | PS[%][2] |
|---|---|---|---|---|---|---|---|
| 9 | — | 50 | 8.3 | 1.3 | 91.0 | 0.053 | 3.9 |
| 10 | 100 | 50 | 8.8 | 1.1 | 90.4 | 0.059 | 3.4 |

[1] MeH: methyl hydrogen dichlorosilane MeHSiCl$_2$, Di: dichlorodimethylsäure Me$_2$SiCl$_2$; Tri/Di: (trichloromethylsilane MeSiCl$_3$/dichlorodimethylsilane Me$_2$SiCl$_2$); the percentages (% by weight) are based on the monomer obtained
[2] PS: polysiloxanes [boiling point (at 1013 mbar) >80° C.] th percentage relates to the total quantity of silane mixture formed.

The results in Table 3 demonstrate that, in the presence of tin-containing promoters, halogen- and/or alkoxy-containing sulphur compounds have a positive effect on the production rate and lower the percentage of MeH and of high-boiling compounds.

Example 4

This example demonstrates the effect of a combination of halogen- and/or alkoxy-containing sulphur compounds (SOCl$_2$ was selected as an example) and aluminum as a promoter (for example in the form of Cu$_9$Al$_4$) on the results obtained in the Rochow reaction.

The same silicon was used as in example 1.

TABLE 4

The addition of halogen- and/or alkoxy-containing sulphur compounds and aluminum to the contact material

| test no. | sulphur added [ppm] | aluminum added [ppm] | production rate [g/h][1] | MeH [%][1] | Di[%][1] | Tri/Di[1] | PS[%][2] |
|---|---|---|---|---|---|---|---|
| | — | 50 | 5.5 | 2.1 | 88.0 | 0.074 | 3.0 |
| | — | 100 | 6.0 | 2.3 | 87.7 | 0.072 | 4.4 |
| | 100 | 50 | 5.9 | 1.4 | 89.8 | 0.066 | 1.5 |

[1] MeH: methyl hydrogen dichlorosilane MeHSiCl$_2$: Di: dichlorodimethylsilane Me$_2$SiCl$_2$; Tri/Di: (trichloramethylsilane MeSiCl$_3$/dichlorodimethylsilane Me$_2$SiCl$_2$); the percentage (% by weight) are based on the monomers obtained
[2] PS: polysiloxane [boiling point (at 1013 mbar) >80° C.], the percentage relates to the total quantity of silane mixture formed The results in Table 4 demonstrate that, in the presence of aluminum, halogen- and/or alkoxy-containing sulphur compounds considerably reduce the content of high-boiling compounds and produce a reduction in MeH and a high production rate.

We claim:

1. In the preparation of an alkyl halogen silane by reacting silicon with an alkyl halide in the presence of at least one catalyst, the improvement which comprises effecting the reaction in the presence of at least one easily volatile or gaseous halogen- or alkoxy-containing sulphur compound and optionally at least one additional promoter substance.

2. The method according to claim 1, wherein the easily volatile or gaseous sulphur compound used is at least one selected from the group consisting of SOCl$_2$, SO$_2$Cl$_2$, SCl$_2$ and S$_2$Cl$_2$.

3. The method according to claim 1, wherein the alkyl halide is methyl chloride.

4. The method according to claim 1, wherein there is present at least one additional promoter substance selected from the group consisting of tin, zinc, phosphorus and aluminum, in elementary form or in the form of a compound thereof.

5. The method according to claim 2, wherein the alkyl halide is methyl chloride, and there is present at least one additional promoter substance selected from the group consisting of tin, zinc, phosphorus and aluminum, in elementary form or in the form of a compound thereof.

* * * * *